(12) United States Patent
Ball

(10) Patent No.: US 6,230,569 B1
(45) Date of Patent: May 15, 2001

(54) USE OF A STREAM OF COMPRESSED GAS TO DETECT SEMICONDUCTOR INTERCONNECT PROBLEMS

(75) Inventor: Michael B. Ball, Boise, ID (US)

(73) Assignee: Micron Technology, Inc., Boise, ID (US)

(*) Notice: Subject to any disclaimer, the term of this patent is extended or adjusted under 35 U.S.C. 154(b) by 0 days.

(21) Appl. No.: 09/317,314

(22) Filed: May 24, 1999

(51) Int. Cl.⁷ ..................................................... G01N 3/08
(52) U.S. Cl. ................................................................. 73/827
(58) Field of Search ................................. 73/827, 842, 37

(56) References Cited

U.S. PATENT DOCUMENTS

| | | | |
|---|---|---|---|
| 3,559,054 | 1/1971 | Bowers | 324/713 |
| 3,581,557 | 6/1971 | Drees et al. | |
| 3,759,088 | 9/1973 | Hardwick | 73/37 |
| 5,085,084 | 2/1992 | Salatino | |
| 5,214,963 | 6/1993 | Widder | 73/827 |
| 5,341,685 | 8/1994 | Malone | 73/827 |

Primary Examiner—Hezron Williams
Assistant Examiner—Jay L. Politzer
(74) Attorney, Agent, or Firm—TraskBritt

(57) ABSTRACT

A method for product assurance for semiconductor devices having wire bonded die and carrier assemblies comprises "puffing" the arc of each bonded wire individually with a stream of gas to force the wire arc into a substantially vertical plane which is positioned laterally away from adjacent wire arcs. The "puff" may be accomplished by a stream of compressed gas from a nozzle positioned beneath the wire or alternatively, by a vacuum drawn from a nozzle positioned above the wire arc, or by both techniques. The force exerted is sufficient to debond defective bonds, break structurally deficient wires and move debonded wires or broken wire ends away from the die, lead frame and other wires. The method is preferably applied just following wire bonding and/or just prior to encapsulation of the die.

32 Claims, 3 Drawing Sheets

USE OF A STREAM OF COMPRESSED GAS TO DETECT SEMICONDUCTOR INTERCONNECT PROBLEMS

BACKGROUND OF THE INVENTION

1. Field of the Invention

This invention relates generally to the fabrication of semiconductor devices. More specifically, the invention pertains to the testing of wire bonds and lead wires, also called bond wires, for integrity.

2. State of the Art

The secure bonding and maintenance of bond wires extending between the bond pads of a semiconductor die and the leads of a corresponding lead frame are critical in the manufacture of semiconductor devices employing this technique. Typically, the method of interconnecting the bond pads of an integrated circuit (IC) device to a lead frame or other carrier having conductive traces comprises individual wire bonding techniques such as thermocompression, thermosonic, or ultrasonic bonding. The wires are typically formed of gold, aluminum, or alloys thereof, and have wire diameters of e.g. 0.001 to 0.003 inch. As wire sizes have become increasingly miniaturized, the inherent strength of the wires and of the wire bonds to the bond pads and leads has necessarily been reduced.

The now-common use of "leads over chip" (LOC) semiconductor die assemblies replaces a traditional lead frame having a central, integral support (commonly called a die-attach tab, paddle, or island) to which the back surface of a semiconductor die is secured, with a lead frame arrangement wherein the dedicated die-attach support is eliminated and at least some of the leads extend over, and are secured to, the active surface of the die. LOC die assemblies may have centrally located bond pads, thus increasing the length of the leads, which may flex during a wire bonding operation.

Because of the high cost of IC devices and the difficulty of correcting defective wire interconnects once the devices are encapsulated, it is vital to achieve a very high degree of reliability during wire bonding. More sophisticated methods and apparatus are required to limit the frequency of wire and wire bond failure.

As well-known in the art, the inadequacy or failure of bond wires and wire bonds may be caused by a wide range of factors, and may result from events occurring (a) at the time of bonding, (b) during assembly steps following bonding but before encapsulation, and (c) during encapsulation.

Inadequately bonded wires may occur because of many reasons, including bond pad surfaces which are not adequately cleaned, incomplete metallization of bond pads, wire impurity, inadequate bonding temperature, stress-strain mismatches, excessive flexing, corrosion, intermetallic grain growth followed by stress-induced creep, as well as by other causes.

The wires themselves may occasionally break because of impurity-induced weakness, corrosion, and mishandling such as an accidental excessive force applied during wire-pull testing.

Wires may also be weakened or fail during die processing steps subsequent to bonding but before encapsulation. Handling of the die during intermediate processing steps such as testing and inspection may result in weakening or separation of inner (to a bond pad) or outer (to a lead or trace) wire bonds as well as occasional breakage of a wire itself.

The step of encapsulating the die with a plastic or ceramic material may also result in wire or bond failure. In transfer molding of a lead frame-mounted semiconductor die, the die is suspended from its active surface from the underside of inner lead extensions of a lead frame (typically Cu or Alloy 42) by a tape, screen print or spin-on dielectric adhesive layer. The bond pads of the die and the inner lead ends of the frame are then conductively connected by wire bonds (typically Au, although Al and other metal alloy wires have also been employed) by means known in the art. When any intermediate steps are completed after wire bonding, the resulting die assembly is placed in a mold cavity and encapsulated in a heated, thermosetting particulate-filled polymer which, upon curing, forms a highly cross-linked matrix no longer capable of being melted. Typically, a post-cure step completes the curing of the polymer. The die and lead frame assembly may comprise the framework of a dual-in-line package (DIP), zig-zag in-line package (ZIP), small outline j-lead package (SOJ), thin small outline package (TSOP), quad flat pack (QFP), plastic leaded chip carrier (PLCC), surface mount device (SMD) or other plastic configuration.

During transfer molding, a defect known as "wire sweep" may become a troublesome problem. In this type of defect, the advancing flow front of liquid thermoset molding compound sweeps the wires against each other, causing short-circuiting. Factors that tend to exacerbate wire sweep include high wire loop heights, long wire bond lengths, bond orientation perpendicular to the advancing polymer flow front, rapid mold compound transfer times, high transfer pressures, rapid viscosity rise of the polymer melt, relatively low wire modulus, and insufficiently bonded wires. The difficulty in precisely controlling all of the above factors results in packaged, yet defective, semiconductor devices which must be discarded at considerable loss.

As is well known in the art, the wires and wire bonds may also fail during or following post-curing because of the stresses formed in the polymer package.

Of course, once the die has been encapsulated by transfer molding, it is very difficult, if even possible, to correct a wire which is broken, shorted, or which has become unbonded from a bond pad or lead finger. Even though the cost of manufacturing a semiconductor device through the encapsulation step is substantial, it is rarely economical to attempt repair of a defective wire or wire bond after transfer molding. Removal of the encapsulant without destroying the interconnecting wires is extremely difficult, particularly when the encapsulant is a transfer-molded filled polymer.

Although the state of the art in wire bonding is continually improving, ever-increasing demands for further miniaturization, increased circuit complexity, enhanced production speed, reduced cost, product uniformity and reliability require further improvements in quality control.

It is apparent that to avoid failure of wires or wire bonds, both the wire modulus and the bond strength should be as high as reasonably possible, given known process parameters. It is thus desirable to provide a method for confirming that prior to encapsulation, all of the wires and/or bonds meet a predetermined minimum value of strength.

One test which is used to determine the wire bond strength comprises the use of a hook to pull a lead wire loop upward with an increasing measured force until a wire bond breaks. This is a destructive test and is not used routinely on production dies.

In a related test, a lead wire is pulled upward by a hook at a minimum threshold force value indicative of satisfactory bonds. Only inadequately bonded leads fail the test, so the test is at least arguably "non-destructive". Wire pull testing is typically conducted under 25×–50× magnification and is a tedious and time consuming task. Further, damage is occasionally incurred by the wire under test, or by adjacent wires. The bond pulling test is not generally appropriate for testing wire bonds of very closely spaced lead wires used in many recently developed semiconductor devices.

U.S. Pat. No. 3,581,557 of Drees et al. briefly indicates the common problem of inadequate bonding of wires to semiconductor die bond pads and package leads. Drees et al. discloses an apparatus for exerting a "puff" of gas substantially transversely across and at a selected angle to each wire following its bonding to break away weakly bonded wires. The test is conducted on each wire immediately after it has been bonded at both ends, so that any failed wires will not be displaced by the relatively horizontal puff of gas into adjacent wires. Thus, the test must be conducted on a lead wire before the next adjacent wire is bonded to the die and lead frame. If the final wire fails in this test, it may be blown into the adjacent first wire and may displace or break that wire as well. Thus, the test has distinct problems if used following completion of multiple wire bonds. In addition, the "puff" duration is severely limited in order to avoid wire vibration induced by the gas stream.

U.S. Pat. No. 5,085,084 of Salatino discloses a method for testing the bond integrity of lead frame leads to bond pads by applying a fluid to the underside of a plurality of leads simultaneously. A conductive sensor is positioned above the leads, and if a lead-to-bond pad bond fails due to the applied fluid force, its broken end is blown upward to contact the sensor and close an electrical circuit. The Salatino method is also disclosed as being applicable to testing of wire bonds.

Several problems are inherent in the Salatino test. First, the actual force exerted on each lead will depend upon the free area for gas flow in the vicinity of the lead. Thus, the width and proximity of adjacent leads will affect the applied force. Both of these factors may be highly variable, not only from die to die, but in respect to the leads on a single die as well. Further, failure of a single lead-to-bond pad bond results in movement of that lead out of the lead pattern, decreasing the resistance to air flow and reducing the force exerted on adjacent leads. Thus, the force is not evenly applied to the leads.

SUMMARY OF THE INVENTION

The present invention comprises a method for aligning and testing integrity of bond wire interconnections extending between the bond pads of a semiconductor die and leads of a lead frame or conductive traces on a carrier substrate such as a circuit board. Broken wires and inadequate bonding of the wire ends are detected at times in the manufacturing process where the wires may be readily replaced, i.e., following bonding and before encapsulation.

In the method of the invention, the upwardly extending "arch" or arc (also commonly termed a "loop") formed by each acceptable bonded wire is motivated upwardly into a generally vertical plane passing through the inner and outer bonds of the wire. Thus, the lateral distance between adjacent bond wires is generally maximized. The upward motivation of defective, i.e. broken or inadequately bonded, bond wires results in their upward movement away from the die, lead frame and other interconnection wires. A broken or debonded wire will not contact an active surface, bond or other wire, thus avoiding short circuiting or damage to other wires.

The method of the invention comprises a quality control procedure which is preferably performed at least two times during the manufacture of a semiconductor device, i.e., 1) following wire bonding to ensure that all bond wires have been securely bonded at both ends by the wire bonding capillary and that no bond wires have broken, and 2) following any intermediate manufacturing steps and handling and prior to die encapsulation, to ensure that the wire bonds and wires have not been damaged between wire bonding and the intended encapsulation of the die in a filled-polymer package by transfer molding, or by other techniques such as so-called "glob topping" with a silicone gel or other viscous encapsulant.

Thus, broken bond wires and/or inadequately bonded wires will be detected and replaced before a badly-bonded die is encapsulated.

Each interconnecting bond wire bonded between the die and lead frame is subjected to an upward fluid force on the underside of the wire arc or arch. The force may be produced by a brief stream of compressed gas from a nozzle positioned beneath the wire arc. Alternatively, a vacuum nozzle closely positioned to the upper side of a ad wire arc may be utilized to draw a wire upwardly. In some cases, a lower compressed gas nozzle and an upper vacuum nozzle may be used in combination to provide a desired upwardly directed force.

The force exerted on the underside of an arc of an interconnection wire is selected to debond an inadequately bonded wire. The method is performed at a time when the defective bond may be reworked at minimum time and expense, or the device discarded before the additional manufacturing expense of encapsulation is expended thereon. The detection and removal of badly wire-bonded dice prior to insertion in the transfer-molding apparatus ensures that only adequately bonded dice are encapsulated.

The method of the invention may also reduce the frequency of incidence of wire sweep because bent and leaning wires are substantially vertically reoriented at, or close to, a maximum separation distance immediately prior to transfer-molding.

The correction of weak bonds prior to encapsulation also reduces failure due to expansion/contraction of the encapsulant during and following encapsulation.

The use of a stream of gas to orient a bond wire upwardly to a maximal arc position overcomes the tendency to bond wire vibration which may occur in lateral "puffing" of the wire, as described in U.S. Pat. No. 3,581,557. Thus, the "puffing" duration is not limited to extremely short periods to avoid wire destruction.

BRIEF DESCRIPTION OF THE SEVERAL VIEWS OF THE DRAWINGS

The invention is illustrated in the following figures, wherein the elements are not necessarily shown to scale.

DETAILED DESCRIPTION OF THE INVENTION

A method and apparatus are provided by the invention for testing the wire bonds of a semiconductor die, wherein (a) a weak or broken bond or wire is identified by completing breakage thereof, (b) strongly bonded wires are aligned in positions at a maximum distance from each other, and (c) wires extending to a failed bond are moved to a vertical orientation away from the active surface of the die, the lead frame, and other wires.

Figure 1:
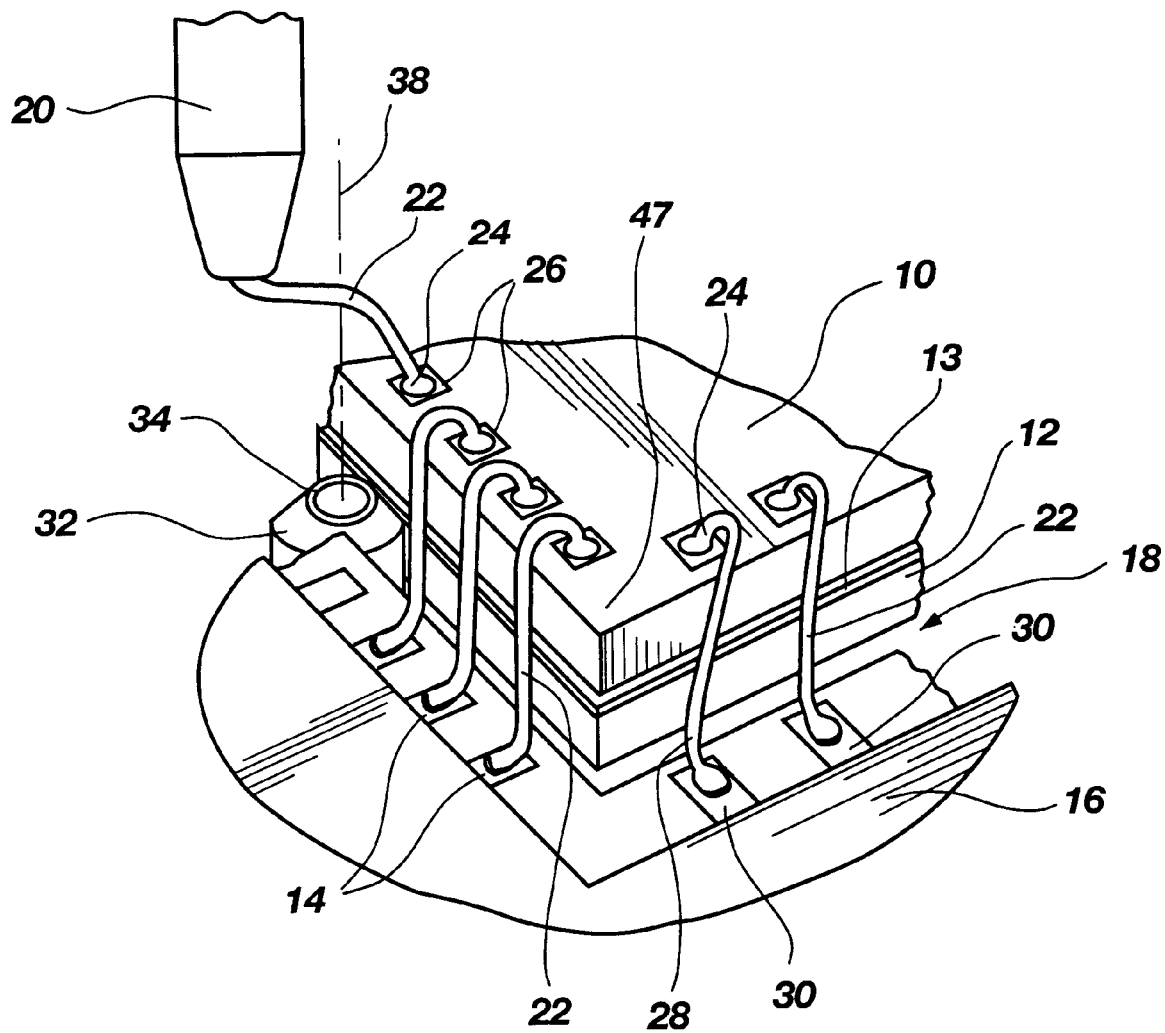
FIG. 1 is a perspective view of an integrated circuit die connected to a lead frame by wire bonding and apparatus of the invention for conducting an alignment-and-test procedure on the wires.
Figure 2:
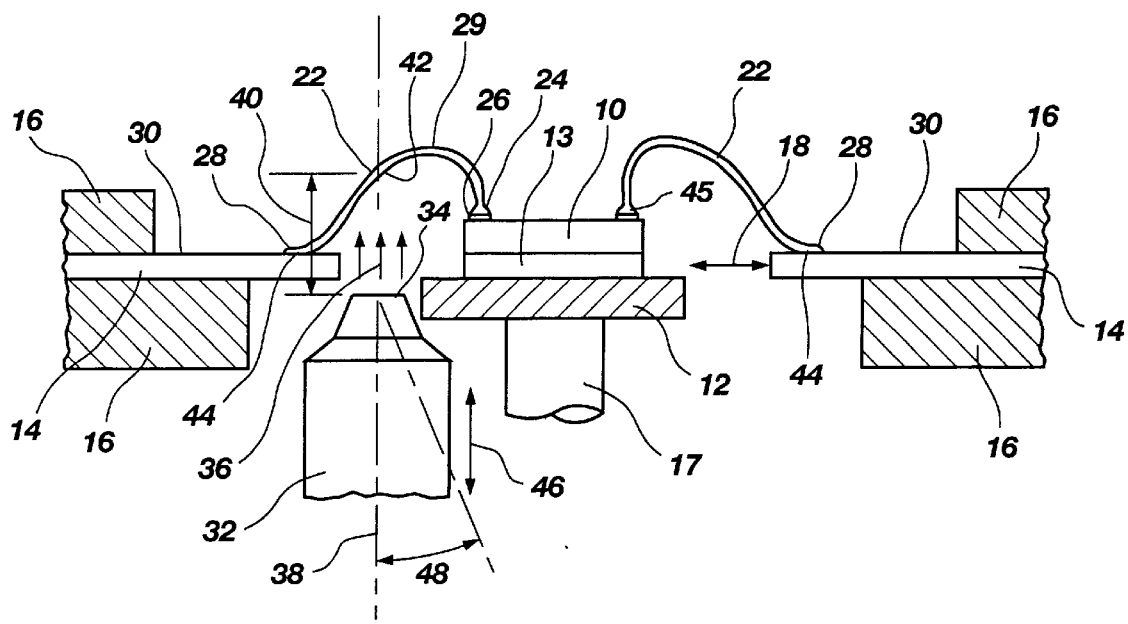
FIG. 2 is a side view of a die and lead frame with apparatus of the invention for conducting an alignment-and-test procedure on the interconnecting wires.

With reference to the drawings, and particularly to FIGS. 1 and 2, a semiconductor die 10 supported on a die paddle 13 of a conventional lead frame 14 is shown on a chuck or other substrate 12 and having leads 30 of the lead frame 14 supported by support members 16, e.g. clamps in a position surrounding the die 10 but separated from it by peripheral space 18. The substrate 12 and lead frame 14 are mounted to be movable in unison, whereby wires 22 may be sequentially bonded between the die 10 and the lead frame 14. A bonding tool 20, shown as a wire feeding capillary, is used to bond the wire 22 to a bond or die pad 26 of the die 10 and a lead 30 of the lead frame 14. The bonding tool 20 comprises a capillary for thermocompression or thermosonic bonding, or a wedge for ultrasonic bonding. Conventional interconnecting conductive wires 22 have inner ends 24 shown as being ball-bonded at 45 to peripheral die pads 26 on the die 10, and outer ends 28 wedge-bonded by bonds 44 to leads 30 of the lead frame 14.

In a first embodiment of the invention shown in FIGS. 1 and 2, a compressed gas nozzle 32 is selectively positioned beneath a bond wire 22. An upwardly directed stream 36 of gas is provided through a nozzle orifice 34 of nozzle 32 and in an orientation along line 38 to exert an upward force on the underside 42 of the bond wire 22 (e.g. the inside of the wire "arc" or "arch"). The nozzle 32 and wire 22 are aligned so that (a) the wire will generally bisect the gas stream 36 and (b) the distance 40 from the nozzle orifice 34 to the wire 22 is within a relatively narrow range for each wire undergoing the operation. Given these constraints, the fluid force exerted on each tested wire 22 meets the test criteria.

The nozzle 32 is configured to move in a horizontal (x-y) plane for alignment with each wire 22 in turn. In addition, the nozzle 32 is moveable in a vertical direction 46 to provide the desired proximity 40 to the underside 42 of the wire 22 undergoing the test. Furthermore, the nozzle 32 is moveable to a limited degree from the vertical position. Thus, the nozzle 32 may be positioned at an angle 48 of up to about 30 degrees from the vertical in any direction, so that a wire 22 on any side of the die 10 may be subjected to a selectively-angled fluid force aligning it in a generally vertical plane, or in a somewhat non-vertical plane to place the wire 22 at a maximum distance from adjoining wires 22. Such selectivity may be useful, for example, with interconnecting wires 22 adjacent the die corners 47.

The stream 36 of gas is directed at the underside 42 of the wire 22 at a sonic or subsonic velocity at which a laminar flow regime is established, as is well-known in the field of fluid flow dynamics. The velocity may be varied (alone or in conjunction with proximity to the wire) to achieve a desired minimum test force, depending upon the wire diameter, wire modulus, required bond strength, wire length, wire-to-orifice distance 40, and other factors. The optimum velocity may be calculated from the above factors, or determined by testing.

The method of the test comprises mounting the die 10 and lead frame 14, supported respectively by chuck 12 and clamps 16, on a bonding machine pedestal 17 and conductively bonding the inner end 24 and outer end 28 of a bond wire 22 to a die pad 26 and lead 30 of the lead frame 14, respectively, forming an arc, arch or loop 29 therebetween. A central portion of the arc 29 of the wire 22 is subjected to a generally brief upward burst of fluid force to align the arc 29 of a firmly bonded wire 22 into a vertical plane passing through said inner and outer ends of the wire. Should either or both of the wire bonds 44, 45 be too weak to withstand the fluid force, i.e. separate from the die pad 26 or lead 30, the defectively connected wire 22 will be forced by the gas stream 36 upwardly and away from the die 10, lead frame 14 and other interconnecting wires 22 bonded to the die and lead frame. Likewise, ends of a broken wire 22 will similarly be blown upwardly.

The "central portion" of the wire 22 is defined as comprising approximately the middle 80 percent of the wire between the respective inner and outer ends 24, 28.

Figure 3:
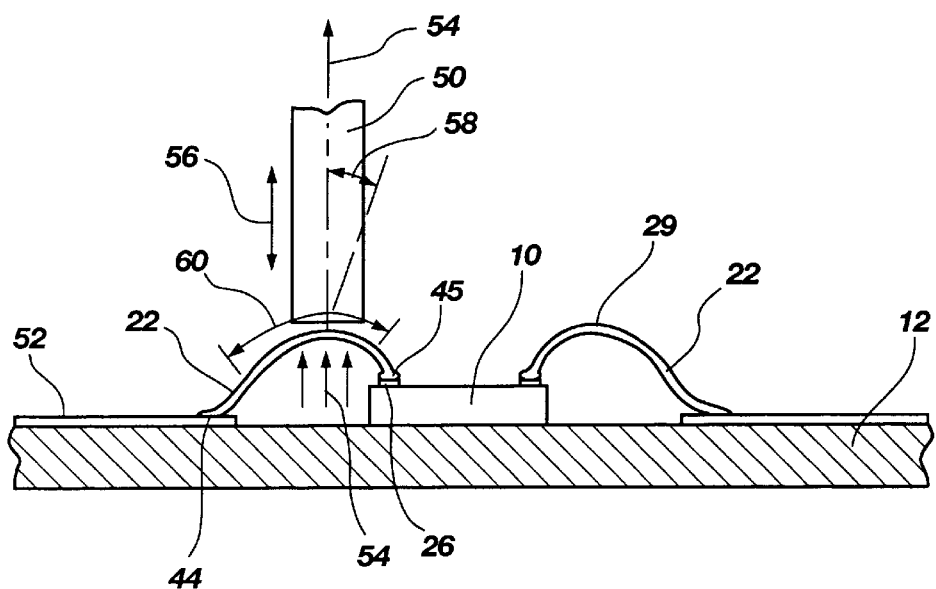
FIG. 3 is a side view of a die and lead frame with apparatus of another embodiment of the invention for conducting an alignment-and-test procedure on the interconnecting wires.

Another form of apparatus for performing the invention is illustrated in FIG. 3. A die 10 is shown attached to a carrier substrate 12 which may be e.g. a circuit board with lead traces 52 of a lead frame. Such a configuration, termed "chip on board" or "COB," is conventionally used when a plurality of dice is back-bonded to a substrate and then wire bonded, as in fabrication of memory modules. In this instance, there is insufficient access space to place a compressed gas nozzle beneath the wires 22. Interconnection wires 22 are shown bonded to die pads 26 by bonds 45 and to the lead traces 52 with bonds 44. A substantially vertically oriented vacuum nozzle 50 is positioned immediately above a bonded wire 22 for drawing a vacuum for a short time period. The vacuum nozzle 50 draws an upward stream 54 of gas past a central portion 60 of the wire 22, drawing it upward. As a result, (a) adequately bonded wires 22 are aligned in a generally vertical plane separated from adjacent wires 22, and (b) inadequately bonded wires 22 are separated at a bond site and moved upward away from the die 10, lead traces 52 and other wires 22. The defective bonds may thus be readily identified, and the wires removed and replaced. Again, broken wires 22 will also be clearly identified by their elongated, free ends.

The vacuum nozzle is moveable vertically in direction 56, in a horizontal plane, and at an angle 58 from the vertical of up to about 20 degrees.

The typical force useful for aligning and testing a 1–3 mil. diameter gold wire may, for example, be about 1–4 grams and more preferably, about 1.5–2.5 grams force. Such a force will align an adequately bonded wire in the desired vertical plane, and debond and position a defectively bonded wire, or a broken wire, upwardly away from potential short-circuiting or damage caused by inappropriate contact with other bond wires 22, bond pads 26, or traces 52.

The time during which a gas stream 36 is blown against the wire 22, or a vacuum is drawn above a wire, is desirably as brief as possible to maintain a high production rate. Thus, the wire 22 may be "puffed" for, e.g., about 0.1 second to no more than several seconds. However, there is no set time limit imposed by induced detrimental wire vibration, as in a prior art test method using substantially laterally oriented puffs. Thus, for example, the force may be continuously applied while a broken wire or one having a defective bond is being removed, to facilitate projection thereof above the other wires 22.

It should be recognized that the embodiment of FIG. 3 is also especially applicable to testing bond wires and wire bonds in an LOC die and lead frame configuration, since such a configuration necessarily places the arcs, arches or loops 29 of the bond wires 22 over the active surface of the die (since the leads extend onto the die), preventing placement of a nozzle 32 under the wires 22.

Figure 4:
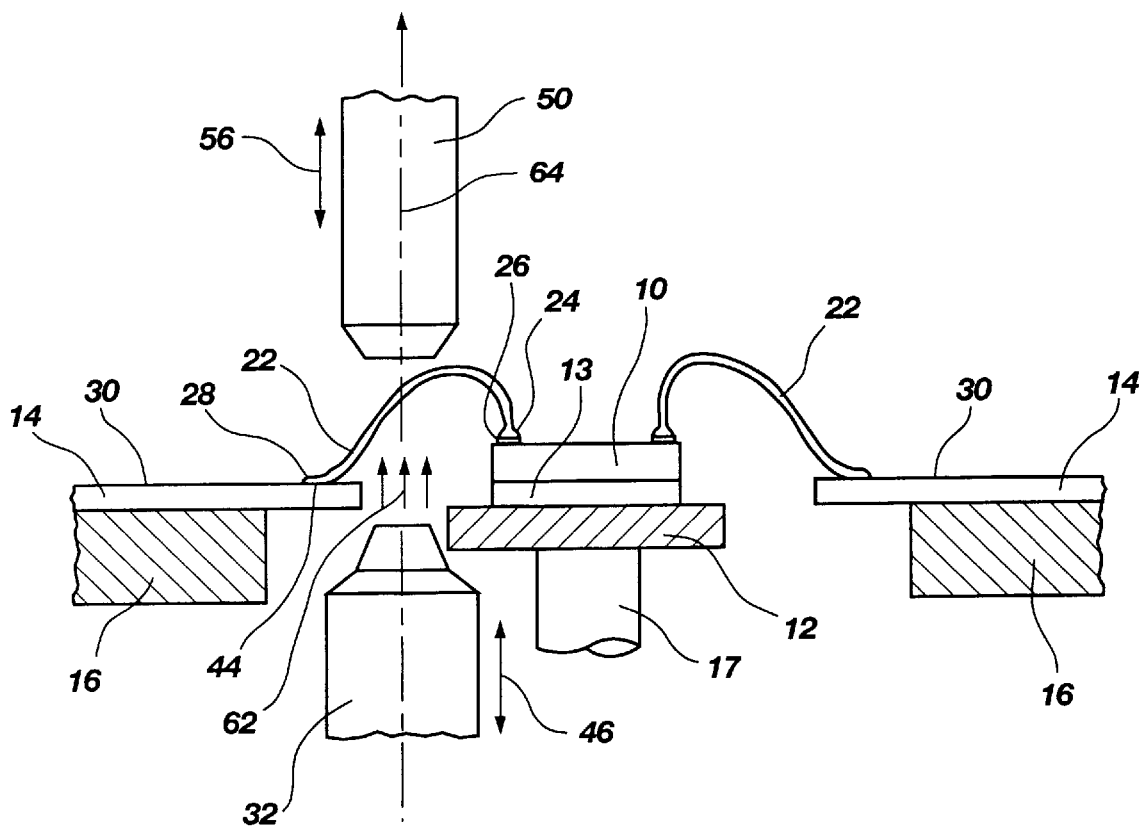
FIG. 4 is a side view of a die and lead frame with apparatus of a further embodiment of the invention for conducting an alignment-and-test procedure on the interconnecting wires.

In another version of the apparatus useful in this invention and as shown in FIG. 4, a test apparatus may include both a compressed gas nozzle 32 positioned below a wire 22, and a vacuum nozzle 50 positioned above the wire. The wire 22 may be subjected to an upward gas stream from the compressed gas nozzle 32 as in FIG. 2, to an upward gas stream from a vacuum nozzle 50 as in FIG. 3, or to an upward gas stream 62 effected by use of both nozzles concurrently or sequentially. In the latter mode and when concurrent flow is employed, the two nozzles 32, 50 are aligned along centerline 64 to provide a coherent laminar stream 62 of gas. The force exerted on the wire 22 may be more accurately controlled through the use of both nozzles.

It is significant that the operation of this invention may be conducted at two separate times during manufacture of the semiconductor device. First, use of the method immediately following the wire bonding step (of each individual wire or of all wires collectively) ensures that all wires are adequately bonded prior to further handling and, possibly expensive intermediate manufacturing steps such as testing. Second, use of the method following any intermediate steps but prior to encapsulation, e.g. in a filled-polymer package by transfer molding, ensures that any bond/wire damage is corrected and the wires are optimally aligned before the encapsulation step.

As described herein, the invention provides a nondestructive quality assurance method which reveals defects and inadequate bonding of wires to a semiconductor die and to a lead frame or traces on a carrier substrate such as a circuit board. The method may be applied to various die and lead frame configurations as described herein, without limitations including the aforementioned LOC configurations and chip-on-board (COB) assemblies. In the latter, wire bonds are formed between the bond pads of the dice and conductive traces on the board. Thus, the method may be applied before the die-and-board assemblies are "globtopped" e.g. with a silicone gel or an epoxy, or otherwise encapsulated, as by potting.

It is apparent to those skilled in the art that various changes and modifications may be made in the methods of testing wires and wire bonds between any type of semiconductor die and a lead frame or carrier substrate as disclosed herein without departing from the spirit and scope of the invention as defined in the following claims.

What is claimed is:

1. A method for in-process quality assurance of a semiconductor device including a die and a lead or trace pattern, comprising:
    mounting a semiconductor die having a lead or trace pattern associated therewith on a wire bonding machine pedestal;
    conductively bonding an inner end of at least one wire to said semiconductor die;
    conductively bonding an outer end of said at least one wire to a portion of said lead or trace pattern, said at least one wire being formed in an upwardly extending arc between said inner and outer ends of said at least one wire; and
    subjecting an underside of at least a central portion of said arc to an upward burst of fluid force to align said arc of said at least one wire into a substantially vertical plane passing through said inner and outer ends if said at least one wire is firmly bonded at said inner and outer ends, and to force at least a portion of said at least one wire upwardly if said at least one wire is inadequately bonded or is structurally deficient.

2. The method of claim 1, further comprising the step of removing said semiconductor die and associated lead or trace pattern from said wire bonding machine pedestal following said conductively bonding said inner and outer ends of said at least one wire.

3. The method of claim 1, wherein the step of subjecting the underside of the at least a central portion of said arc of said at least one wire to an upward burst of fluid force comprises a release of a brief upward stream of a compressed gas from a nozzle disposed beneath said arc of said at least one wire.

4. The method of claim 3, wherein said brief upward stream of compressed gas imposes on the at least said central portion of said arc of said at least one wire a pressure representative of the force absorbable by an adequately bonded, structurally sound wire without resultant damage thereto.

5. The method of claim 4, wherein said at least one wire comprises a 1 to 3 mil. diameter gold wire, and said brief upward stream of compressed gas imposes on said arc of said at least one wire an upwardly directed pressure resulting in application of 1 to 4 grams of force on said at least said central portion of said arc of said at least one wire.

6. The method of claim 4, wherein said at least said central portion of said arc of said at least one wire is exposed to said brief upward stream of compressed gas for a period greater than 1 second.

7. The method of claim 4, wherein said brief upward stream of compressed gas is oriented within about 30 degrees of vertical.

8. The method of claim 4, wherein said brief upward stream of compressed gas is substantially vertical in direction.

9. The method of claim 1, further comprising the steps of:
    identifying said at least one wire as being defective or defectively bonded during said upward burst of fluid force;
    continuing to subject said at least one wire to said upward burst of fluid force to maintain at least a portion of said at least one wire in a vertical orientation;
    removing said at least one wire;
    stopping said upward burst of fluid force; and
    bonding a new wire to said die and said lead or trace pattern portion.

10. The method of claim 9, further comprising the step of subjecting at least a central portion of said bonded new wire to a brief upward burst of fluid force to test said bonded new wire.

11. The method of claim 1, wherein the step of subjecting the underside of the at least a central portion of said arc to an upward burst of fluid force comprises applying a brief period of upward suction from a vacuum nozzle closely positioned above said arc of said at least one wire.

12. The method of claim 11, wherein the step of subjecting the underside of said at least said central portion of said arc to an upward burst of fluid force comprises the steps of:
    positioning said vacuum nozzle proximate and above said arc;
    applying a vacuum through said vacuum nozzle to draw said arc toward said vacuum nozzle;
    withdrawing said vacuum nozzle upwardly to draw said arc to a substantially full vertical height; and
    if an inadequate bond of said at least one wire is identified or if said at least one wire is structurally deficient, withdrawing said vacuum nozzle upwardly to a position beyond said substantially full vertical arc height to draw at least a portion of said at least one wire upwardly.

13. The method of claim 11, wherein said upward suction imposes on said underside of said at least the central portion of said arc of said at least one wire a pressure representative of a force absorbable by an adequately bonded, structurally sound wire without resultant damage thereto.

14. The method of claim 11, wherein said at least one wire comprises a 1 to 3 mil. diameter gold wire, and said upward suction imposes on said arc an upwardly directed pressure equivalent to 1 to 4 grams of force on the underside of the at least said central portion of said arc.

15. The method of claim 11, wherein said underside of said at least said central portion of said arc is exposed to said brief period of upward suction for a period greater than 1 second.

16. The method of claim 11, wherein said brief upward period of upward suction is substantially vertical in direction.

17. The method of claim 11, further comprising the steps of:
identifying said at least one wire as defective or defectively-bonded;
continuing to subject said at least one wire to said brief period of upward suction to maintain at least a portion of said at least one wire in a vertical orientation;
removing said at least one wire;
stopping said upward burst of fluid force; and
bonding a new wire to said die and said lead or trace pattern position.

18. The method of claim 17, further comprising the step of subjecting at least a central portion of said bonded new wire to a brief upward burst of fluid force to test said bonded new wire.

19. The method of claim 1, wherein said outer end of said at least one wire is bonded to a lead of a lead frame.

20. The method of claim 1, wherein said outer end of said at least one wire is bonded to a conductive trace on a circuit board.

21. The method of claim 1, wherein the step of subjecting the underside of the at least a central portion of said arc of said at least one wire to said upward burst of fluid force comprises the simultaneous release of an upward stream of a compressed gas from a nozzle beneath said arc and application of suction from a vacuum nozzle positioned above said arc of said at least one wire.

22. The method of claim 1, wherein the step of subjecting the underside of the at least a central portion of said arc of said at least one wire to said upward burst of fluid force comprises the sequential release of a brief upward stream of a compressed gas from a nozzle beneath said arc and a burst of suction force from a vacuum nozzle positioned above said arc of said at least one wire.

23. The method of claim 1, further comprising the steps of:
performing at least one intermediate handling, fabrication or testing step on said semiconductor device following wire bonding of said at least one wire and prior to encapsulation of said semiconductor die;
repeating testing of said at least one wire and said conductive bonds of said at least one wire by subjecting a central portion of said arc of said at least one wire to a burst of fluid force prior to encapsulation;
repairing and repeat testing of any defective wire bonds uncovered by said testing; and encapsulating said semiconductor die.

24. The method of claim 23, wherein said semiconductor die is encapsulated in a filled-polymer package by transfer molding.

25. An apparatus for testing structural and bond integrity of wires interconnecting a semiconductor die with a lead or trace pattern, said apparatus comprising:
a support structure for said semiconductor die and said lead or trace pattern;
a nozzle mounted below said semiconductor die and said lead or trace pattern, said nozzle positioned vertically below and between said semiconductor die and at least a portion of said lead or trace pattern, for exerting a predetermined upward fluid force on at least central portions of an arc of a wire bonded to said semiconductor die and said lead or trace pattern by emitting a compressed gas from said nozzle; and
a mechanism for changing relative positions of said support structure and said nozzle for sequentially subjecting each of a plurality of bonded wires to said upward fluid force.

26. The apparatus of claim 25, wherein said nozzle is substantially vertically oriented.

27. An apparatus for testing structural and bond integrity of wires interconnecting a semiconductor die with a lead or trace pattern, said apparatus comprising:
a support structure for said semiconductor die and said lead or trace pattern;
a first nozzle mounted above said semiconductor die and said lead or trace pattern, said first nozzle positioned vertically above said semiconductor die and a portion of said lead or trace pattern, for exerting a predetermined upward suction force on at least a central portion of an arc of a wire bonded to said semiconductor die and said lead or trace pattern by drawing a vacuum through said first nozzle; and
a mechanism for changing relative positions of said support structure and said first nozzle for sequentially subjecting each of a plurality of bonded wires to said upward suction force.

28. The apparatus of claim 27, wherein said first nozzle is substantially vertically oriented.

29. The apparatus of claim 27, further comprising means for vertically moving said first nozzle between a position proximate said arc of said wire, a second position wherein said wire arc is fully expanded upwardly, and a third position higher than full expansion of said wire arc.

30. The apparatus of claim 27, further comprising:
a second nozzle mounted below said semiconductor die and said lead or trace pattern, said second nozzle positioned vertically below and between said semiconductor die and a portion of said lead or trace pattern, for exerting a predetermined upward fluid force on the at least the central portion of said arc by emitting a compressed gas therefrom;
a control device configured for operating said first and second nozzles; and
a mechanism for changing the relative positions of said support structure and said second nozzle for sequentially subjecting each of said plurality of bonded wires in sequence to said upward fluid force.

31. The apparatus of claim 30, wherein said control device is configured for operating said first and second nozzles simultaneously.

32. The apparatus of claim 30, wherein said control device is configured for operating said first and second nozzles independently.

* * * * *